United States Patent [19]

Hamilton, Sr. et al.

[11] 4,139,017
[45] Feb. 13, 1979

[54] FLUID FLOW CONTROL AND MOUNTING THEREOF

[76] Inventors: Louis F. Hamilton, Sr.; Louis F. Hamilton, Jr., both of R.R. 1, Box 85D, Weatherford, Okla. 73096

[21] Appl. No.: 822,391

[22] Filed: Aug. 8, 1977

[51] Int. Cl.² ............................................... F16K 7/06
[52] U.S. Cl. .................................. 137/343; 24/135 R; 251/8; 339/95 R; 339/263 R
[58] Field of Search ............ 339/263 R, 263 E, 264 R, 339/95 R; 24/135 R, 135 K, 135 L, 263 A; 251/7-9; 269/243; 137/343

[56] References Cited

U.S. PATENT DOCUMENTS

| 950,111 | 2/1910 | Miner | 251/8 |
|---|---|---|---|
| 1,810,901 | 6/1931 | Bormann et al. | 339/95 R |
| 3,544,060 | 12/1970 | Stoltz et al. | 251/9 |

FOREIGN PATENT DOCUMENTS

| 595673 | 7/1925 | France | 251/8 |
|---|---|---|---|
| 643812 | 9/1950 | United Kingdom | 24/135 R |

Primary Examiner—Martin P. Schwadron
Assistant Examiner—Richard Gerard
Attorney, Agent, or Firm—Fishburn, Gold & Litman

[57] ABSTRACT

A fluid flow control and mounting thereof retains a flexible tube in a constant position relative to a stationary structural member and selectively constricts the tube to control the flow of a working fluid transmitted therethrough. The flow control includes an anvil engaged by the tube and a mounting connected to the anvil for detachably connecting the same to a structural member. The anvil has a transversely curved surface with a transverse concave groove therein for receiving and securely yet detachably positioning and retaining the tube therein. Flow control members are movably mounted on a rod extending from the anvil surface and include a slidably mounted clamping disc engageable with a tube positioned in the groove and an adjustment knob movably mounted on the rod. The clamping disc has a roughened surface for frictionally engaging the tube and an opposite smooth bearing surface for engagement with the adjustment knob. The adjustment knob is movable toward the clamping disc to move the same toward the anvil and is retractable to permit the same to be slid away from the anvil. Movement toward the anvil applies pressure to the slidable clamping disc to face the same toward the anvil and controllably compress the flexible tube between the clamping disc and the anvil groove.

5 Claims, 5 Drawing Figures

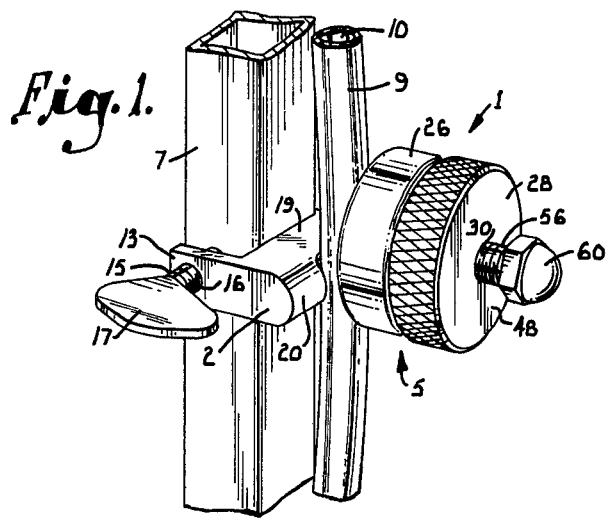
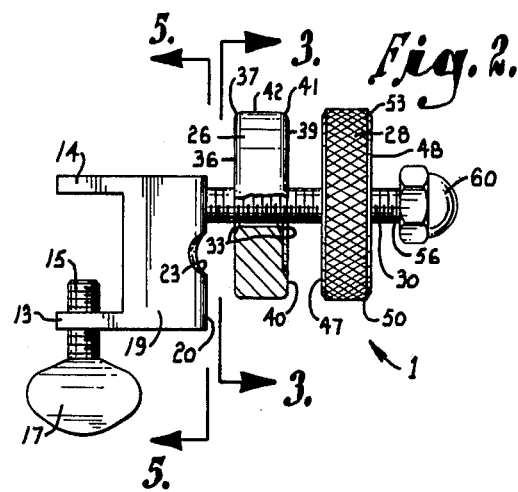
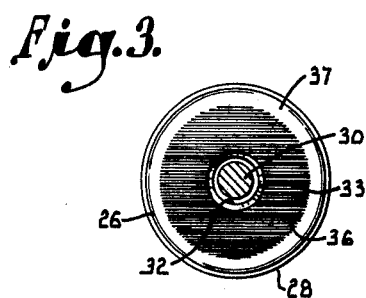
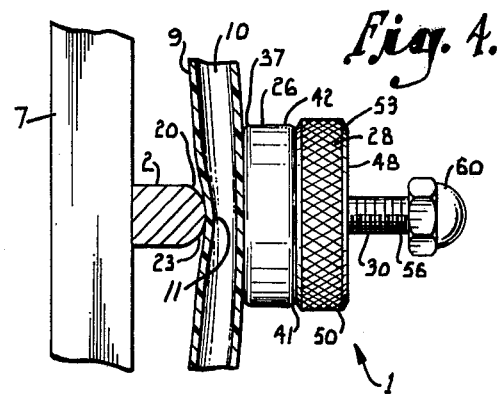
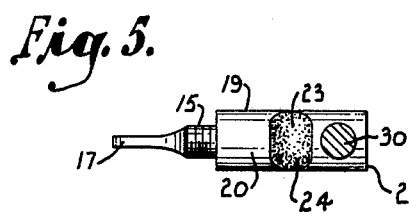

FLUID FLOW CONTROL AND MOUNTING THEREOF

This invention relates to fluid flow controls and mountings thereof and particularly to such devices for retaining and compressing flexible tubes to precisely control the rate of flow therethrough.

Various types of clamping and fluid flow controlling devices for constricting flexible tubes are well known in the art and used, for example, in industrial, laboratory and medical applications. These devices are often unsatisfactory because they seldom permit sufficiently precise regulation of fluid flow and commonly rely on constricting pressure merely to retain the tube. These devices often loosen once set and allow the flow to increase and even more significantly, upon movement of the portion of the tube extending beyond the device, can suddenly completely close off and stop the flow of fluid. These devices commonly employ opposing broad, flat, clamping jaw surfaces between which the tube is positioned. Upon pressure to the jaws, the corners thereof cause a pair of constrictions in the tube passage adjoining the corners which make the tube susceptible to closure upon movement. Also, the two constrictions unnecessarily make accurate regulation of flow and compression of the tube difficult.

Should a device such as set forth above be used for example, in connection with a dialysis machine supplying lifesupporting fluids to a patient, the problems become readily apparent. The procedure calls for occasional changes of fluid sources and the device must be easily used to stop flow when switching sources. The process takes several hours and the device must maintain a set flow over that period. Most importantly, should the tube become completely closed, tragic results could occur.

The present invention seeks to overcome the above difficulties and provides a fluid flow control and mounting thereof which retains a tube securely yet detachably retained in control means without excessive constricting pressure thereon. The control means employs tube receiving surfaces which create a single point of constriction, thereby facilitating ease of adjustment and precise regulation of fluid transmission without unscheduled flow changes or stoppages. For instance, in the use of the present invention in connection with a dialysis machine, the flow rate once set remains set until changed by the operator. The tube passage could not suddenly close unintentionally and stop the flow of vital bodily fluids.

In view of the above, the principal objects of the present invention are: to provide a fluid control and mounting device having means detachably connecting same to suitable stationary structural members; to provide such a device for receiving and securely yet detachably retaining a flexible tube therein; to provide such a device for receiving a flexible tube therein without puncturing or otherwise harming the same; to provide such a device for selectively compressing a flexible and compressible tube retained thereby for controlling the flow of fluids transmitted therethrough; to provide such a device for precisely setting a desired flow rate and having the set rate remain constant without unscheduled rate changes; to provide such a device having bearing means facilitating operation thereof; and to provide such a device which is relatively inexpensive, highly reliable in use and well adapted for its intended purpose.

Other objects and advantages of this invention will become apparent from the following description taken in connection with the accompanying drawings wherein are set forth by way of illustration and example, a certain embodiment of this invention.

FIG. 1 is a perspective view illustrating a tube retaining fluid control and mounting thereof embodying this invention which is attached to a representative structural member.

FIG. 2 is an elevational view of the fluid flow control and mounting, portions of which are broken away to reveal certain details.

FIG. 3 is a fragmentary view of the fluid flow control and mounting taken along lines 3—3, FIG. 2 and shows certain features thereof.

FIG. 4 is an elevational view of the fluid flow control and mounting attached to a structural member and having a flexible tube received therein, wherein portions are broken away to reveal the relative positions of the flow control and the tube.

FIG. 5 is a fragmentary view of the fluid control and mounting thereof taken along lines 5—5, FIG. 2 and shows certain features thereof.

Referring more in detail to the drawings:

As required, a detailed embodiment of the present invention is disclosed herein, however, it is to be understood that the disclosed embodiment is merely exemplary of the invention which may be embodied in various forms. Therefore, specific functional and structural details disclosed herein are not to be interpreted as limiting, but merely as a basis for the claim and as a representative basis for teaching one skilled in the art to variously employ the present invention in virtually any appropriately detailed structure.

The reference numeral 1 generally indicates a fluid control and mounting thereof embodying the present invention, comprising a tube retaining anvil 2 connected to a bracket or mounting 3 and a flow control or engagement means 5 associated with the anvil 2.

FIG. 1 illustrates the fluid flow control and mounting thereof 1 detachably connected to a stationary structural member 7 which, for example, represents a segment of various fluid emitting industrial, laboratory, or medical appliances, such as a dialysis machine, or the support members associated therewith. As illustrated herein, the fluid flow control and mounting thereof 1 receives and securely yet detachably retains a flexible tube 9 extended from the appliance and selectively controls or regulates the flow of fluid transmitted through a passage 10 in the tube 9. The tube 9 is comprised of virtually any material commonly used in the manufacture of resilient tubing, such as polyethylene, polypropolene, PVC, or other suitable material usable with the fluid flowing therethrough, and is preferably constructed of flexible and compressible material. To gain the full advantages of this invention, a flexible tube is desired which can be laterally compressed, closing the passage 10, and upon release of the compressive forces, return to its prior dimensions. Plastic or rubber tubes and the like are preferred for this application. The fluid flow control and mounting thereof 1 is constructed of virtually any suitable material which is sufficiently strong to withstand the shear and bending forces applied thereto, such as steel, brass, aluminum or the like. The particular type of material used preferably depends upon the intended environment of use, for example, when associated with tubes transmitting saline solutions, a rust and corrosion resistant material such as stainless steel is desired.

For detachably connecting the anvil 2 to the stationary structural member 7, a bracket or mounting 3 is included therewith. It is to be understood that various types of mounting means, such as clips, bolts, or the like may be employed depending upon the shape of the structure to which the anvil 2 is to be connected. In the illustrated structure, the mounting 3 includes a pair of embracing arms 13 and 14 integrally constructed with the anvil portion 2 and engageable with opposite sides of the structural member 7. As illustrated the arm 13 has a threaded bore 16 through which a threaded bolt or fastener 15 rotatably extends. To facilitate manual rotation, the fastener 15 includes a winged head 7 providing grasping portions to rotate the fastener 15 into engagement with the structural member 7.

The anvil 2 comprises a generally rectangular block 19 which has a curved or arced surface 20 extended longitudinally thereon. As illustrated, the surface 20 has a concavely arcuate, longitudinally curved groove 23 extending transversely across the mid-portion thereof. Preferably, the groove 23 has a roughened surface 24 for frictionally engaging the tube 9 and is appropriately sized to substantially conform to the dimensions of an arcual segment of a tube to be positioned therein and retain the same transversely aligned relative to the longitudinal axis of the surface 20. The double curvature of the groove 23 as described above not only provides a recess into which the tube 9 is positioned but includes a curvature over which the tube 9 is bent and compressed by the engagement means 3 described below. The centrally located apex of the curve provides a single point 11 or area of constriction for precisely controlling the passage of fluids therethrough. This single point 11 also facilitates ease of compression and, being centrally located, prevents inadvertant closure of the passage 10 upon small lateral movements of the tube 9.

Fluid flow control or engagement members 5 are mounted to the anvil 2 and extend therefrom for engaging securely yet detachably retaining the tube 9 in combination with the groove 23. The working portions of the illustrated engagement members 5 include a pair of inflexible and translatable discoidal members respectively depicted herein as comprising a slidable clamping disc 26 and a rotatable adjustment knob 28 threadably mounted on a threaded bolt or rod 30 extending from the anvil 2. The rod 30 extends from an epicentral portion of the curved surface 20 and is spaced from the groove 23 a slight distance so as to align the clamping disc 26 adjoining and parallel to a tube 9 positioned in the groove 23. The clamping disc 26, in this example, includes an axially aligned bore 32 which has an inside diameter slightly greater than the diameter of the rod 30 to permit the clamping disc 26 to slide reciprocally on the rod 30 between the anvil 2 and the knob 28. This reciprocating and sliding movement allows the clamping disc 26 to embrace a tube 9 positioned in the groove 23 and remain rotationally stationary relative thereto.

In operation, the adjustment knob 28 rotates downwardly against the clamping disc 26 to move the same toward the anvil 2 to engage and controllably compress the tube 9 and back to permit the clamping disc 26 to be slid away from the anvil 2. The clamping disc 26, being slidable on the rod 30, does not tend to rotate when engaged with the tube 9 and therefore prevents twisting of the tube 9 in the groove 23 which distorts the passage 10.

The clamping disc 26 includes a pair of chamfered edges 33 at the respective outlets of the bore 32 to aid in reciprocatory movement. As illustrated in FIG. 2, the disc 26 extends radially beyond the transversely positioned groove 23 and overlies a portion of the curved surface 20 to provide sufficient area to engage the tube 9 therebetween. The curved surface 20 extends beyond the disc 26 and provides an ample area on which to position the tube 9. To aid in engaging the tube 9, the clamping disc 26 has a slightly roughened anvil-side surface 36 for frictional engagement therewith. The clamping disc 26 also includes a chamfered margin or edge 37 to prevent cutting or otherwise damaging the tube 9.

To facilitate ease of adjustment, the clamping disc 26 includes an opposite surface 39 shaped for smoothly abutting rotation with the adjustment knob 28. In the illustrated example, the surface 39 includes a circular planar bearing member or ridge 40 providing a low friction turning surface and which maintains the clamping disc 26 in a wobble-free and parallel relationship when abutting the knob 28. A chamfered edge 41 formed on the peripheral margin of the surface 39 smoothly adjoins the rim 42 of the clamping disc 26 and also aids smooth rotation of the knob 28 on the disc 26.

The adjustment knob 28 has an axially aligned threaded bore 45 rotatably mounting the knob 28 on the threaded rod 30 to be rotatably tightenable upon the slidable clamping disc 26. In the illustrated structure, the knob 28 is discoidal in shape and includes smoothly finished opposite surfaces 47 and 48 with a side or rim 50 extending therebetween. A pair of chamfered surfaces 53 provide smoothly finished transitional edges between the surfaces 47 and 48 and the rim 50. Preferably, the knob 28 has a marginal dimension slightly greater than that of the clamping disc 26 to aid in grasping and rotating the knob 28 without inadvertantly also rotating the disc 26. To further aid in grasping and turning the knob 28 without rotating the clamping disc 26, the rim 50 has a knurled surface, while the rim 42 of the disc 26 is smoothly finished. To retain the clamping disc 26 and the knob 28, the illustrated example employs retaining means in the form of a cap nut 60 mounted on the outermost end 56 of the rod 30.

In the employment of this invention, as illustrated in FIGS. 1 and 4, the user first connects the mount 3 to a suitably situated stationary structural member 7 to support the device. The engagement means 5 is opened to receive the tube 9 by rotating the adjustment knob 28 toward the upper end 56 and sliding the clamping disc 26 against the knob 28. Next, the flexible tube 9 is positioned over the curved surface 20 of the anvil 2 and into the groove 23. Then the clamping disc 26 is slidably translated toward the tube 9 to frictionally engage the same. To maintain the disc 26 in position, the adjustment knob 28 is grasped and rotated toward the disc 26 and into slidable and parallel abutting relationship with the bearing surface 39 of the clamping disc 26. The knob 28 is controllably rotated or tightened, directing the clamping disc 26 toward the anvil 2 and applying pressure to the tube 9. When it is desired to lessen the flow of fluid, the knob 28 is further rotated toward the anvil 2 to bend and compress the tube 9 in the groove 23 and constrict the passage 10. The rate of flow may be controlled or regulated by varying the amount of tigthness or degree of rotation of the adjustment knob 28 and therefore the degree of compression of the tube 9 to selectively constrict the passage 10 to the extent that the flow of fluids may be stopped entirely when desired. The flow is increased and/or the tube 9 removed by reversing the above recited steps. The mount 3 is loosened and detached from the structural member 7 and the clamp 1 transported to a remote location for storage.

It is to be understood that while one form of this invention has been illustrated and described, it is not to be limited to the specific form or arrangement of parts herein described and shown, except insofar as such limitations are included in the following claims.

What is claimed and desired to secure by Letters Patent is:

1. A fluid flow control and mounting thereof for retaining a tube in a constant position relative to a stationary structural member and for selectively constricting said tube to control the flow of a working fluid flowing from a source thereof through a passage in said tube, said fluid flow control and mounting thereof comprising:
   (a) an anvil having an anvil surface for engagement by a tube;
   (b) a mounting connected to said anvil, said mounting being detachably connectible to a stationary structural member for retaining said anvil in a constant position relative to said structural member;
   (c) said anvil surface including a concave groove positioned transversely thereto for receiving said tube said groove being curved longitudinally and having a roughened surface for frictional engagement by a tube;
   (d) a rod spaced from said groove and extending from said anvil surface;
   (e) engagement members movably mounted on said rod in parallel and engaging relationship to said anvil surface and extending over said groove whereby said engagement members selectively compress said tube and constrict said passage;
   (f) said engagement members respectively comprising discoidally shaped adjustment knob and clamping disc;
   (g) said adjustment knob and said clamping disc respectively including peripheral margins; and
   (h) the peripheral margin of said adjustment knob extending a slight distance beyond the peripheral margin of said clamping disc for facilitating grasping and rotation of said adjustment knob over said clamping disc.

2. A fluid flow control and mounting thereof as set forth in claim 1 wherein:
   (a) said anvil extends outwardly beyond said clamping disc peripheral margin.

3. A fluid flow control and mounting thereof as set forth in claim 2 wherein:
   (a) said clamping disc includes a roughened surface whereby said tube is frictionally engageable between said roughened surface of said groove and said roughened surface of said clamping disc.

4. A fluid flow control and mounting thereof as set forth in claim 3 wherein:
   (a) said clamping disc includes a circular planar bearing member for smooth rotation thereon by said adjustment knob.

5. A fluid flow control and mounting thereof as set forth in claim 4 wherein:
   (a) said clamping disc includes an axially aligned bore having chamfered outlet portions thereof, thereby facilitating movement of said clamping disc on said rod.

* * * * *